United States Patent [19]

Sato

[11] Patent Number: 4,819,255
[45] Date of Patent: Apr. 4, 1989

[54] STEREO X-RAY FLUOROGRAPHY APPARATUS

[75] Inventor: Hideki Sato, Nasu, Japan

[73] Assignee: Kabushiki Kaisha Toshiba, Kawasaki, Japan

[21] Appl. No.: 116,158

[22] Filed: Nov. 3, 1987

[30] Foreign Application Priority Data

Nov. 19, 1986 [JP] Japan ................. 61-273892

[51] Int. Cl.$^4$ ............................................. A61B 6/02
[52] U.S. Cl. ....................................... 378/42; 378/41; 378/99; 358/111
[58] Field of Search ................. 378/41, 42, 62, 98, 378/99; 358/111, 91, 92

[56] References Cited

U.S. PATENT DOCUMENTS

| | | | |
|---|---|---|---|
| 4,214,267 | 7/1980 | Roese et al. | 378/42 |
| 4,544,949 | 10/1985 | Kurihara | 378/42 |
| 4,578,802 | 3/1956 | Itoh | 378/41 |
| 4,654,699 | 3/1987 | Medina | 358/92 |

FOREIGN PATENT DOCUMENTS

| | | | |
|---|---|---|---|
| 0142751 | 5/1985 | European Pat. Off. | 378/41 |
| 56-168484 | 12/1981 | Japan . | |

*Primary Examiner*—Craig E. Church
*Assistant Examiner*—David P. Porta
*Attorney, Agent, or Firm*—Finnegan, Henderson, Farabow, Garrett, & Dunner

[57] ABSTRACT

A stereo X-ray fluorography apparatus includes a stereo X-ray tube having right and left focal points for irradiating a subject, in alternate fashion, with X-rays, a television camera for picking-up right and left images, resulting from the X-rays emitted from the right and left focal points, after the passage of the X-rays through the subject, a television monitor for alternately displaying the right and left images picked-up by the television camera, and a pair of glasses for allowing light to be alternately transmitted and not transmitted, repetitively and in synchronism with the switching of the displaying of the right and left images on the television monitor. For the television monitor, use is made of a double-rate (120 fields per second) type. The images are picked-up by the television camera, upon the subject being irradiated with X-rays from the stereo X-ray tube, for every two fields of the television camera. The picked-up images are stored in frame memories, in synchronism with the X-ray irradiation, and the right and left field images are alternately read out from the frame memories for each ½ field period of the TV camera, four times for the respective image, and transmitted to the double-rate television monitor.

9 Claims, 6 Drawing Sheets

STEREO X-RAY FLUOROGRAPHY APPARATUS

BACKGROUND OF THE INVENTION

This invention relates to a stereo X-ray fluorography apparatus for performing a stereo-fluorographic examination through viewing a subject by means of emission of X-rays alternately from right and left focal points of a stereo X-ray tube.

For performing a conventional X-ray diagnostic examination of the circulatory system, such as an angiographic examination of the brain, the heart and abdomen, an X-ray diagnostic apparatus is currently employed which can rapidly perform separate direct and indirect X-ray examinations.

In order to further enhance the diagnostic capacity in the case of angio-cardiography and coronary artery photography, considerable effort has been made to three-dimensionally examine the intricate spatial distribution of the blood vessels, by means of cinematic X-ray photography performed either in a plurality of directions or simply in two directions (using two X-ray tubes)

FIG. 1 shows a conventional X-ray fluorography apparatus for stereo-fluorographically examining a subject by means of exposure of X-rays alternately from two focal points of a stereo X-ray tube. FIG. 2 shows a signal waveform diagram.

Stereo X-ray tube 1 has two focal points located at a predetermined interval apart from each other and from which X-rays are emitted in alternate fashion. At the time of fluorography, a stereo X-ray image, a conventional continuous X-ray is not emitted, but a pulse-like X-ray, which is used in X-ray photography, is emitted alternately from the two focal points of the stereo X-ray tube, so that the subject may be alternately irradiated with X-rays from the right and left focal points. The emission of the X-rays from X-ray tube 1 is controlled by X-ray controller 18 which is made up of stereo X-ray tube control unit 2, high voltage generator 3, and X-ray control unit 4. The X-ray irradiation condition is automatically controlled so as to obtain optimal brightness. A high voltage is delivered from high voltage generator 3, through stereo X-ray tube control unit 3, atternately to right and left focal points of X-ray tube 1. The application of the high voltage and alternate emission of the X-rays from the right and left focal points, as described above, are controlled by an X-ray exposure trigger signal g. In FIG. 2, L1, R1, . . . show first X-ray exposure trigger signals from the left and right focal points, . . . , respectively.

The X-ray emitted from X-ray tube 1 passes through subject 5 and is supplied to image intensifier 6 where it is converted to a visible light image (fluorographic image). The fluorographic image is supplied to TV camera 8 through optical distributor 7 equipped with an image formation lens. With cinecamera 13 attached to optical distributor 7, stereo-cinephotographs can be taken through a predetermined operation of optical distributor 7. Fluorography unit 19 is made up of image intensifier 6, optical distributor 7, TV camera 8, and cinecamera 13.

TV camera control unit 9 is connected to TV camera 8 from which it is supplied with a video signal f, to allow the observation of the X-ray fluorographic image. Control unit 9 supplies a signal in synchronism with a vertical synchronizing signal of the video signal f to X-ray control unit 4, which in turn supplies the X-ray exposure trigger signal g to stereo X-ray tube control unit 2.

Control device 4 conveys a signal in synchronism with the vertical synchronizing signal to stereo glass control unit 11, which, on the basis of this signal, in turn drives a pair of glasses 12. The respective lenses of glasses 12 are each made up of a liquid crystal shutter to which a polarizing sheet is attached. Therefore, the transmittance of the lens is electrically varied either to allow the passage or block the passage of incoming light. Unit 11 supplies complementary transmitting and non-transmitting control signals h, i to left- and right-eye lenses, in synchronism with every TV field, so that the images of X-rays emitted from the right and left focal points of X-ray tube 1, after their transmittance through the subject, are observed only through the right- and left-eye lenses, respectively.

In this way, the synchronization of the X-ray irradiation with the TV field and stereo glasses 12 is achieved, so that X-ray irradiation is performed at a rate of 60 times per second, with the alternate switching of the left- and right-eye lenses being performed at a cycle of 1/60 (second). In this way, it is possible to observe the visualized image as a stereo image through the pair of glasses.

In practice, because of the image persistence phenomenon which occurs in the image pickup tube of a TV camera, the image emitted from the focal point on one side of the stereo X-ray tube persists faintly while a new image appears in the next TV field, with the result that it appears overlapping this image, which is emitted from the focal point on the other side of the stereo X-ray tube. Consequently, it is difficult for the operator to view the image as a stereo image. In addition, flickering of the main image is liable to occur, due to the alternate switching of the images emitted from the left and right focal points of the stereo X-ray tube.

SUMMARY OF THE INVENTION

It is accordingly an object of this invention to provide a stereo X-ray fluorography apparatus for performing stereo-fluorographic examination by means of emission of X-rays, in alternate fashion, onto a subject, from two (left and right) focal points of a stereo X-ray tube, in which one image resulting from X-rays emitted from one focal point can be prevented from overlapping an image resulting from X-rays emitted from the other focal point, as a result of the image persistence phenomenon which occurs in image pickup tubes, so that a stereo image can be obtained.

Another object of this invention is to provide a stereo X-ray fluorography apparatus which can prevent the flickering of an image resulting from the switching of right and left images.

A stereo X-ray fluorography apparatus according to this invention comprises an X-ray tube having right and left focal points, a television camera for picking up images, for a predetermined field cycle, corresponding to X-rays passed through a subject, an X-ray tube control unit for allowing the subject to be alternately irradiated, for a period of m fields (m being a positive integer not less than 2) of a TV camera, with X-rays emitted from the right and left focal points of the X-ray tube, and frame memories for storing images, which are picked up by the television camera, at a rate of one per period of m fields, in synchronism with the X-ray irradiation, and for alternately reading out the right and left images thus stored.

DETAILED DESCRIPTION OF THE PREFERRED EMBODIMENTS

A stereo X-ray fluorography apparatus according to one embodiment of this invention will be explained below with reference to the accompanying drawings.

Figure 1:
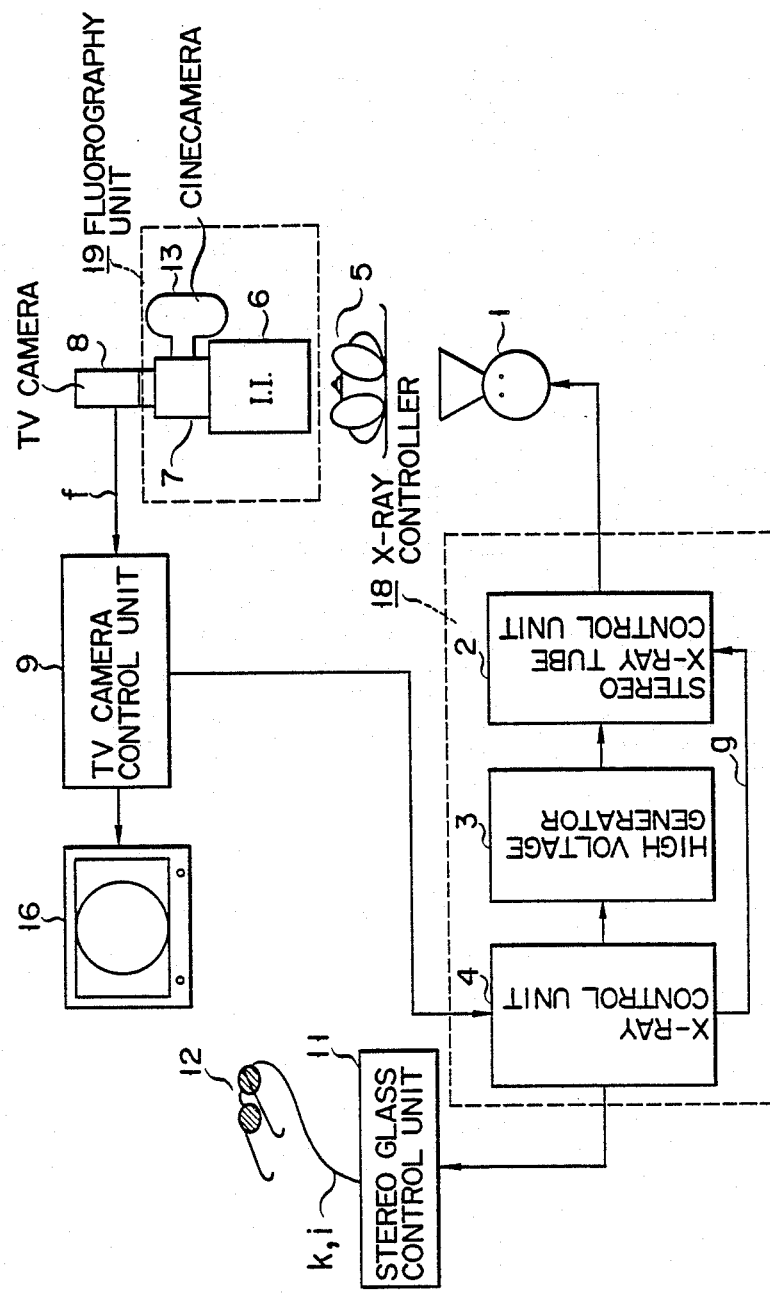
FIG. 1 is a block diagram showing a conventional stereo X-ray fluorography apparatus.
Figure 2:
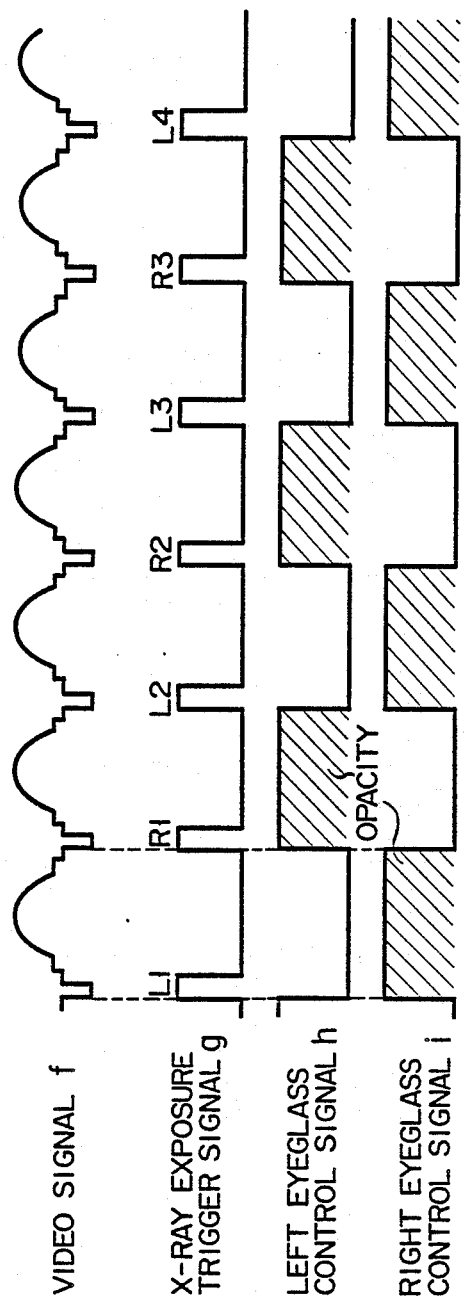
FIG. 2 is a signal waveform diagram for explaining the operation of the conventional apparatus of FIG. 1.
Figure 3:
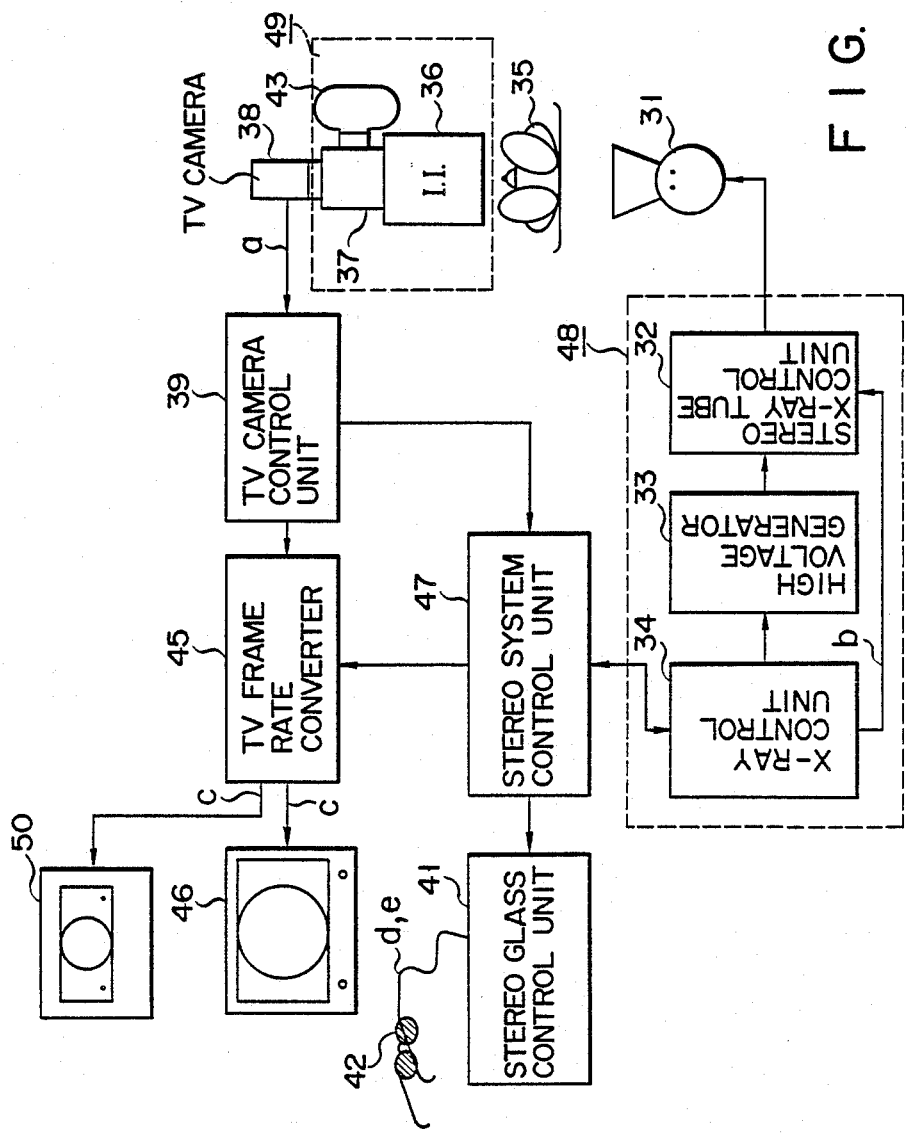
FIG. 3 is a block diagram showing a stereo X-ray fluorography apparatus according to an embodiment of this invention.

As shown in the block diagram of FIG. 3, this embodiment includes, as in the conventional apparatus, stereo X-ray tube 31, X-ray controller 48, fluorography unit 49, TV camera control unit 39, TV monitor (first TV monitor) 46, stereo glass control unit 41 and a pair of stereo glasses 42 and further includes, unlike the conventional apparatus, TV frame rate converter 45, stereo system control unit 47 and second TV monitor 50.

Stereo X-ray tube 31 has a pair of focal points (right and left focal points) arranged at a predetermined interval and emits an X-ray alternately from the right and left focal points. Instead of the two focus type stereo X-ray tube, two separate X-ray tubes may be employed one for one focal point and one for the other focal point.

The emission of the X-ray from X-ray tube 31 is controlled by X-ray controller 48 formed of stereo X-ray tube control unit 32, high voltage generator 33, and X-ray control unit 34. The high voltage generated from high voltage generator 33 is applied, through stereo X-ray tube control unit 32, alternately to the right and left focal points of X-ray tube 31. The application of the high voltage and alternate emission of the X-ray from the right and left focal points are controlled by X-ray control unit 34. As distinct from the conventional one, the X-ray irradiation is performed for at least two fields, not for one field of the TV camera. Since a residual image of an X-ray emitted from one focal point fully disappears in a period of one field, the use of a two-field scheme is desirable for the motion of an image to be substantially faithfully reproduced as that of a fluorographic image. Viewed from the standpoint of reducing an amount of X-ray irradiation, through the fluorographic image is moved awkwardly in an "animation" fashion, the X-ray irradiation may be carried out for every three or more fields. In this way, there is no possibility that a stereo-vision will be disturbed due to an overlap of an image of an X-ray emitted from one focal point with an image of an X-ray emitted from the other focal point in the stereo X-ray tube.

The X-ray with which human subject 35 has been irradiated is converted by image intensifier 36 to a visualized (fluorographic) X-ray image, which is fed through optical distributor 37 including an image formation lens to TV camera 38 where it is picked-up. TV camera 38 is of an ordinary TV camera type whereby that image is picked-up at a rate of 60 fields per second. With cinematic camera 43 attached to optical distributor 37, stereo-cinephotographs can be taken through the predetermined operation of optical distributor 37. Image intensifier 36, optical distributor 37, TV camera 38 and cinematic camera 43 form fluorography unit 49.

TV camera control unit 39 is connected to TV camera 38 and a video signal from TV camera 38 is sent through TV frame rate converter 45 to first TV monitor 46 for normal fluorography and to second TV monitor 50 for freezing any instant fluorographic image. TV monitors 46, 50 are of such a double-rate TV monitor type that an image is displayed at a rate of 120 fields per second. TV frame rate converter 45 permits the image signal coming from TV camera 38 to be written at a rate equal to the signal transfer rate and that image signal to be read out at double the write-in rate. Even if the right and left images are alternately switched for display, the switching rate becomes double on the double-rate field TV monitors in comparison with the conventional switching rate, thus reducing a tendency for a display image to be disturbed due to the occurrence of a flicker.

Here the field frequency ratio between TV camera 38 and TV monitors 46, 50 may never be restricted only to the aforementioned double rate, that is, may be made at more than one (including a fraction thereof) times the rate in which case the TV frame rate converter 45 has the corresponding write-in and read-out rate.

Figure 4:
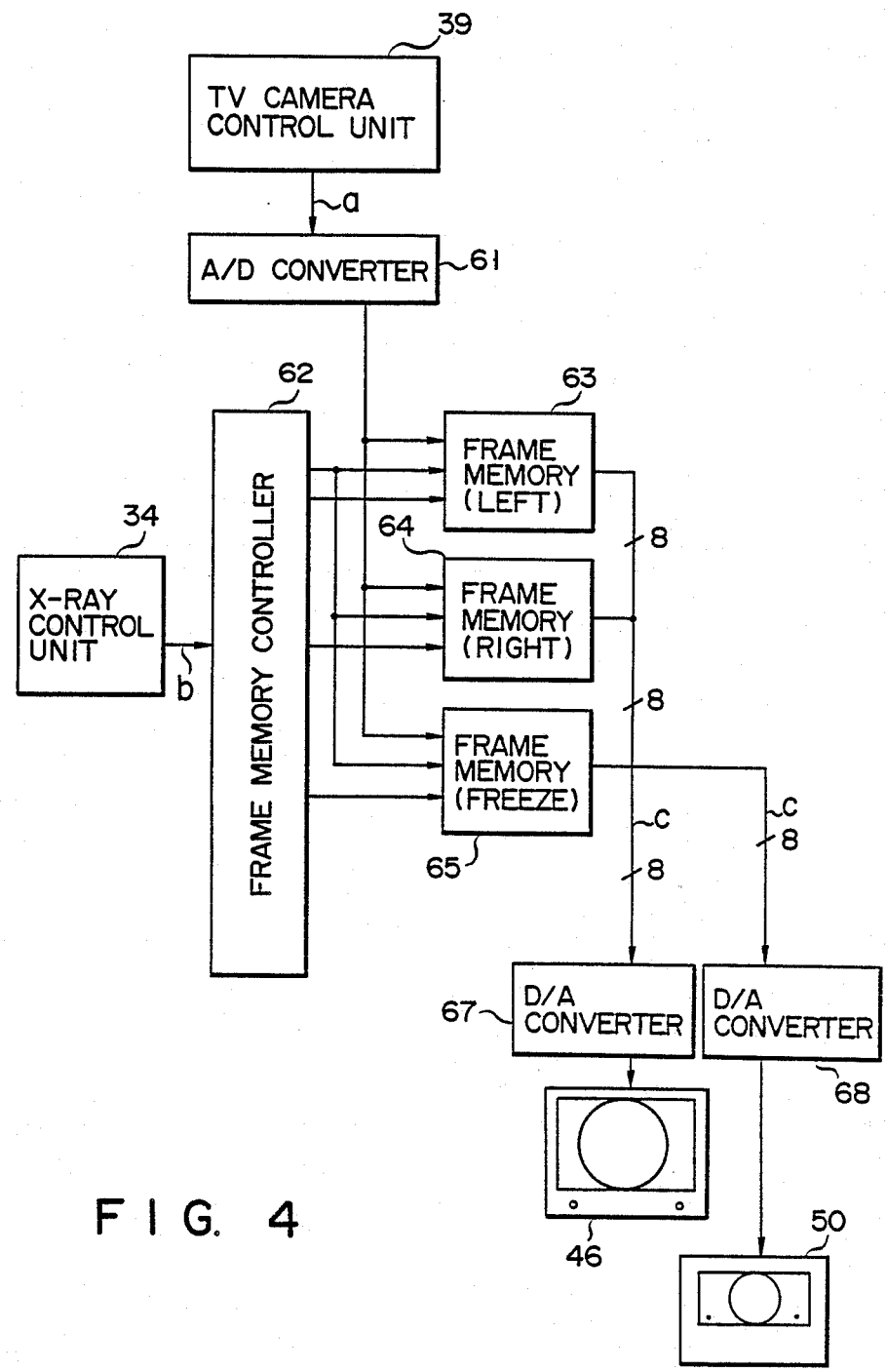
FIG. 4 is a block diagram showing a TV frame rate converter of FIG. 3.

FIG. 4 is a block diagram showing a detailed arrangement of frame rate converter 45. An analog video signal coming from TV camera control unit 39 is converted by A/D converter 61 to a digital video signal. Digital video signals (field signals) corresponding to the irradiation X-rays from the left and right focal points are stored in first and second frame memories (one frame: two fields) 63 and 64. Initial left and right X-ray digital video signals which are obtained after the closure of a switch, not shown, are stored in third frame memoy 65 for freezing. Frame memory controller 62 changes control modes on the basis of signals of three modes from stereo system control unit 47, one for a normal mode at the time of normal-fluorography (not stereo), one for a stereo mode at the time of stereo-fluorography, and one for cine-mode at the time of cine-photography. Frame memory controller 62 controllably reads respective left and right field image signals, four times in total, out of memories 63, 64 and 65 at the double the field frequency of TV camera 38 in an alternate fashion, as appreciated from the X-ray irradiation to be made for every two fields.

The left and right field video signals as alternately read out of first and second field memories 63 and 64 are supplied through first D/A converter 67 to first TV monitor 46 for display. Left and right field video signals as read out of third frame memory 65 are supplied through second D/A converter 68 to second TV mmonitor 50 for display a "freeze" image.

Reverting to FIG. 3, stereo system control unit 47 is connected to TV camera control unit 39, TV frame rate converter 45, stereo glass control unit 41, and X-ray control unit 34. Stereo system control unit 47 controls the irradiation timing such that X-rays are emitted in synchronism with a video signal (coming from TV camera control unit 39) to allow the subject to be irradiated with the X-rays alternately from the right and left focal points for every two fields, not for every field of TV camera 38 as in the case of the conventional apparatus.

Figure 5:
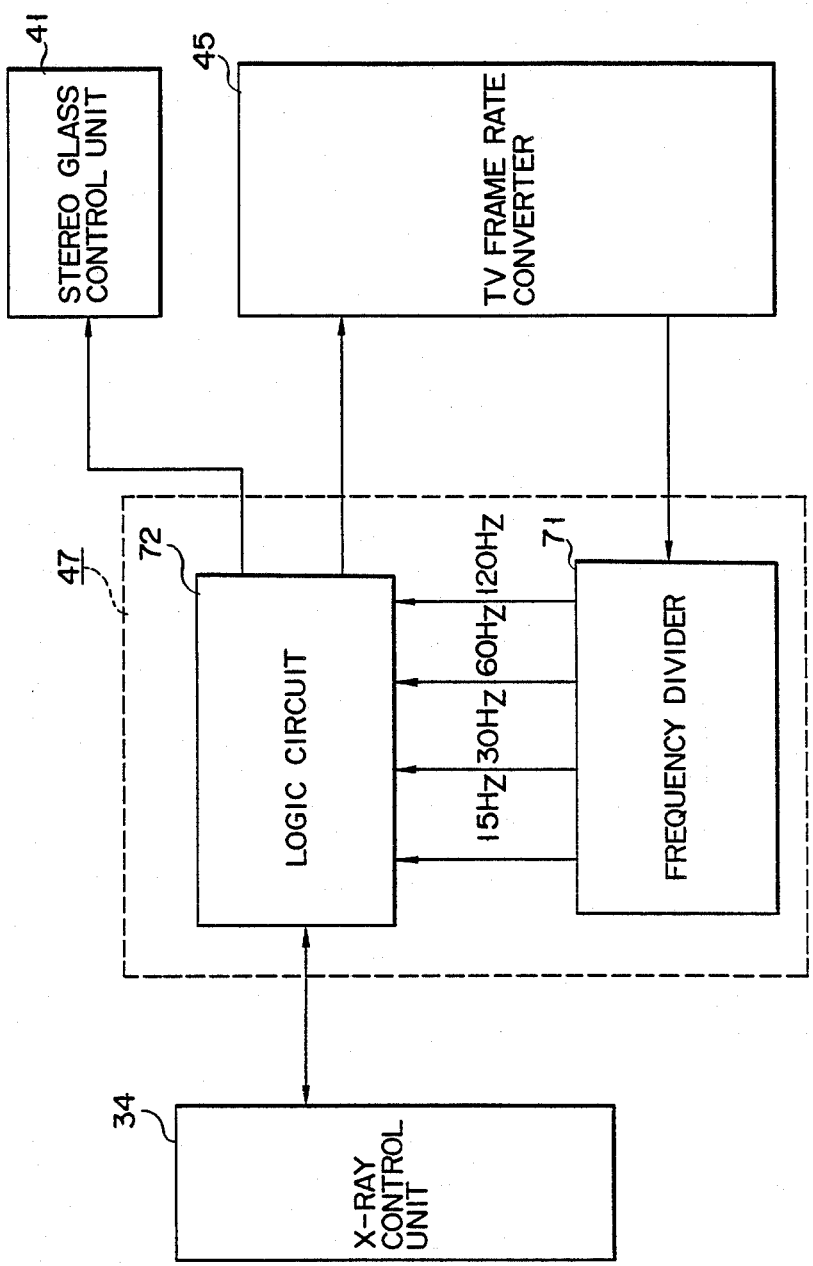
FIG. 5 is a block diagram showing a stereo system control unit of FIG. 3.

FIG. 5 is a block diagram showing a detail of stereo system control unit 47 formed of frequency divider 71 and logic circuit 72. Frequency-divider 71 divides a vertical synchronizing signal from TV frame rate converter 45 into four clock pulses 120 Hz, 60 Hz, 30 Hz, and 15 Hz which are synchronous with the TV camera. These clock pulses are used as an X-ray exposure trigger signal and a drive signal of a pair of stereo eyeglasses. Logic circuit 72 prepares a mode switching signal from a select signal for cinephotography, normal-fluorography and stereo-photography, etc., which is supplied from X-ray controller 34. Stereo system control unit 47 supplies an X-ray exposure trigger signal to X-ray control unit 34 and to stereo X-ray control unit 32 with the use of a mode switching signal from logic circuit 72, field signal for identifying the TV field (odd-/even fields) from TV frame rate converter 45 and clock signal coming from frequency divider 71. Stereo system control unit 47 supplies a drive signal to stereo glass control unit 41 to drive a pair of stereo glasses in synchronization with the double-rate scanning of TV monitor 46.

A pair of glasses 42 have a polarizing sheet attached thereto, which is employed in combination with a liquid crystal unit to allow light to be passed or never passed owing to the electrically varied transmittance of the liquid crystal. That is, with the passage and no passage of light through the respective left- and right-eye lenses alternately repeated for every field of TV monitor 46, a fluorographic X-ray image can be viewed as a stereo-vision.

The fluorographic operation of this embodiment will be explained below with reference to a signal waveform diagram.

Figure 6:
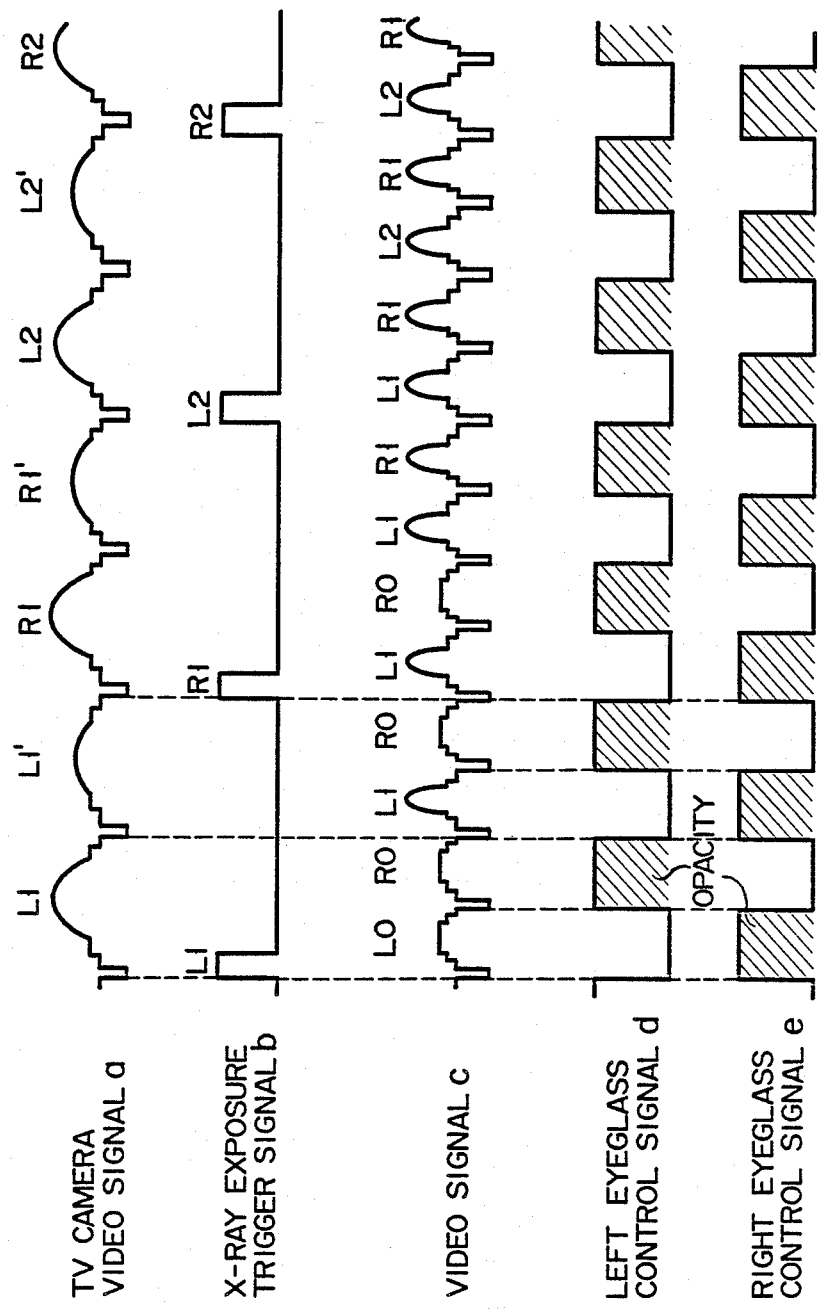
FIG. 6 is a signal waveform diagram for explaining the operation of the embodiment of FIG. 3.

A video signal a of one field per 1/60 second is generated from TV camera 38 irrespective of X-ray irradiation. X-ray control unit 34 supplies an X-ray exposure trigger signal b to a stereo X-ray tube control unit 32 in synchronism with the vertical synchronizing pulse for every two fields. An X-ray is emitted alternately from left and right focal points of stereo X-ray tube 31 for every two fields of TV camera 38. Frame memory controller 62 in TV frame rate converter 45 writes only left and right image signals of a field wherein an X-ray is emitted into left and right frame memories 63 and 64, respectively. In the signal a shown in FIG. 6, L1, R1, . . . without a prime represent those fields to be written into the frame memory and L1', R1', ... with a prime represent those fields never to be written into the frame memory.

On the other hand, frame memory controller 62 alternately reads respective field images, for times, out of frame memories 63 and 64 in that order of L0, R0, L1, R0, L1, R0, L1, R1, L1, R1, L2, R1, ..., in which case the read-out rate corresponds to double the write-in rate.

In synchronism with the read-out of the field images from frame memories 63 and 64, stereo glass control unit 41 controllably supplies the transmitting and non-transmitting control signals d and e to the left- and right-lenses in an alternate fashion so that the fluorographic images of X-rays from left and right focal points of X-ray tube 35 may be observed by left and right eye lenses, respectively.

According to this invention, as set out above, the X-ray exposure is carried out for each plurality of TV fields and the field images thus obtained, once written into the corresponding frame memories, are repetitively read a plurality of times out of the aforementioned corresponding frame memories to compensate for the image signals of the fields in which an X-ray is not emitted. By so doing, in spite of the image persistent characteristic of the image pickup tube in the TV camera, an image of an X-ray emitted from one focal point of the stereo X-ray tube is never overlappingly displayed on an image of an X-ray emitted from the other focal point of the stereo X-ray tube, so that the image can be viewed as a stereo-vision without being disturbed.

Furthermore, by increasing the read-out rate over the write-in rate of the frame memory to obtain a high field frequency, the flickering of an image during an alternate switching of left and right images can be prevented on the double-rate monitor.

This invention is not restricted to the aforementioned embodiment and can be changed or modified in a variety of ways without departing from the spirit and scope of this invention. As the TV monitor use may be made of other types of TV monitors than the double-rate monitor, if the field frequency is high enough such that the flickering can not be recognized. It is only necessary that X-ray exposure be performed for each plurality of fields, a minimum requisite for stereo vision, and the flickering can not be recognized.

What is claimed is:

1. A stereo X-ray fluorography apparatus for stereofluorographically examining a subject by alternately displaying right and left images of X-rays, emitted from right and left focal points, on a screen of display means, and viewing the right and left images through only the right and the left eyes, respectively, said apparatus comprising:

means for picking-up an X-ray image of the X-rays passed through the subject for a predetermined cycle;

means for alternately irradiating the subject with X-rays from said right and left focal points each time an m (m being a positive integer not less than 2) number of images are picked up by said picking-up means; and means for storing said m number of images, at each time of X-ray irradiation, from among those images picked up by said picking-up means, and for supplying the right and left images, which are alternately read out, to said display means.

2. The stereo X-ray fluorography apparatus according to claim 1, wherein sadd storing means has a memory capacity for storing a 2 m number of images, so that said right and left images stored are alternately read out at least m number of times for the respective image.

3. The stereo X-ray fluorography apparatus according to claim 1, wherein said picking-up means comprises a television camera for picking-up field images, said irradiating means alternately emits pulse-like X-rays from said right and left focal points, for every two fields, and wherein said storing means has a memory capacity sufficient for storing signals of two frames.

4. A stereo X-ray fluorography apparatus for stereofluorographically examining a subject by viewing right and left images of X-rays, emitted from right and left focal points, through right and left eyes, which comprises:

irradiating means, having said right and left focal points, for alternately irradiating the subject with the X-rays from the right and left focal points;

image pick-up means for picking-up, for a predetermined cycle, right and left images of the X-rays passed through the subject during the alternate irradiation of the subject with X-rays from the right and left focal points of said irradiating means;

image rate converting means for storing images picked up by said image pick-up means, and reading out the right and left images alternately a predetermined number of times at a high rate n-times (n being a number not less than 1) the rate at which the right and left images are stored;

display means for alternately displaying the right and left images read out of said image rate converting means;

a pair of glasses, having right and left lenses, for allowing light to be alternately transmitted and never transmitted, repetitively and in synchronism with the alternate displaying of the right and left images on displaying means; and stereo-fluorography control means for allowing the subject to be irradiated with the X-ray alternately from the right and left focal points for each m (m being a positive integer not less than 2) number of image pick-up cycles of said image pick-up means.

5. The stereo X-ray fluorography apparatus according to claim 4, wherein said irradiating means is a stereo X-ray tube having said right and left focal points.

6. The stereo X-ray fluorography apparatus according to claim 4, wherein said irradiating means is a pair of X-ray tubes located at said right and left focal points.

7. The stereo X-ray fluorography apparatus according to claim 4, wherein said image pick-up means comprises a television camera for picking up images for every field cycle, said display means comprises a television monitor having a field cycle n-times the field cycle of said television camera, and said stereo-fluorography control means comprises means for alternately emitting X-rays from said right and left focal points for each m number of field cycles of said television camera.

8. The stereo X-ray fluorography apparatus according to claim 7, wherein said television camera picks up images of 60 fields per second, said television monitor displays images of 120 fields per second, and said image rate converting means includes memories for storing four-field images and reads alternately respective right and left field imags, four times in total, for each m number of field cycles.

9. The stereo X-ray fluorography apparatus according to claim 4, wherein said pair of glasses comprises right and left lenses each having a liquid crystal unit to which a polarizing sheet is attached and means for allowing light to be alternately transmitted and not transmitted through the right and left liquid crystal units, in synchronism with the read-out of field images from said image rate converting means.

* * * * *

UNITED STATES PATENT AND TRADEMARK OFFICE
CERTIFICATE OF CORRECTION

PATENT NO. :   4,819,255
DATED      :   April 4, 1989
INVENTOR(S):   Hideki Sato It is certified that error appears in the above-identified patent and that said Letters Patent is hereby corrected as shown below:

Claim 2, column 6, line 52, change "sadd" to
   --said--.

Claim 8, column 8, line 22, change "imags" to
   --images--.

Signed and Sealed this

Fifth Day of June, 1990

Attest:

HARRY F. MANBECK, JR.

*Attesting Officer*          *Commissioner of Patents and Trademarks*